US005232928A

United States Patent [19]

Skiles

[11] Patent Number: 5,232,928

[45] Date of Patent: Aug. 3, 1993

[54] TETRAHYDROISOQUINOLINE AMIDES

[75] Inventor: Jerry W. Skiles, Brookfield, Conn.

[73] Assignee: Boehringer Ingelheim Pharmaceuticals, Inc., Ridgefield, Conn.

[21] Appl. No.: 792,130

[22] Filed: Nov. 14, 1991

Related U.S. Application Data

[63] Continuation of Ser. No. 536,912, Jun. 12, 1990, abandoned, which is a continuation of Ser. No. 385,140, Jul. 25, 1989, abandoned.

[51] Int. Cl.$^5$ ...................... A61K 31/47; C07D 217/16

[52] U.S. Cl. .................................... 514/291; 514/307; 546/90; 546/146; 546/147

[58] Field of Search .......................... 546/146, 147, 90; 514/291, 307

[56] References Cited

U.S. PATENT DOCUMENTS 4,565,819 1/1986 Vincent et al. ...................... 546/146

4,624,962 11/1986 Henning et al. .................... 546/146

*Primary Examiner*—C. Warren Ivy

*Assistant Examiner*—James H. Turnipseed

*Attorney, Agent, or Firm*—D. E. Frankhouser; A. R. Stempel; M-E. M. Timbers

[57] ABSTRACT

Tetrahydroisoquinoline amides having the general structure

IA

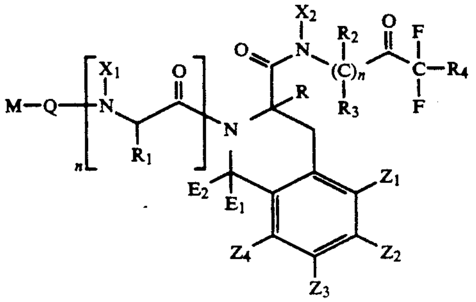

are disclosed, the substituents defined hereinbelow, which amides are useful in inhibiting human leukocyte and neutrophil elastaes.

9 Claims, No Drawings

TETRAHYDROISOQUINOLINE AMIDES

This is a continuation, of application Ser. No. 536,912, filed Jun. 12, 1990, which is a continuation application of Ser. No. 385,140, filed Jul. 25, 1989, both now abandoned.

BACKGROUND OF THE INVENTION

All multicellular organisms comprise material with tensile strength and rigidity, such as bone and collagen, to maintain shape and to facilitate mechanical movement. Additionally, however, such organisms also must comprise a component with intrinsic elasticity, a component that can stretch and then undergo elastic recoil when required. For warm-blooded animals, this elasticity component is an unusually fibrous protein, elastin. Although elastin is present in virtually all tissue in some animals, it comprises an appreciable percentage of all protein in only some tissues, such as the arteries, some ligaments and the lungs. The elastin content of the human lung is about 28%.

Elastin can be hydrolized or otherwise destroyed by a select group of enzymes classified as elastases. The elastases are derived from many tissues in man, including the pancreas, neutrophils, macrophages, monocytes, platelets, smooth muscle cells and firbroblasts. Although called elastase, these enzymes are not just elastin-specific, and have been shown to cleave other proteins.

The role of elastases in normal elastin metabolism is difficult to assess, but a role in protein turnover is assumed. Human neutrophil granulocytes are the source of neutral proteases, human leukocyte elastase (HLE) and human neutrophil elastase (HNE), capable of hydrolysing most connective tissue components. However, the most likely primary physiologic substitute is elastin.

THE INVENTION

This invention relates to new chemical compounds having valuable pharmaceutical activity. In particular the present invention relates to certain tri- and difluoromethyl ketone amide derivatives which are inhibitors of human neutrophil elastase HNE and HLE, which property makes such compounds useful whenever such inhibition is desired. For example, such compounds may be useful in the treatment of tissue degenerative diseases. Additionally, such inhibitors could be used in the diagnosis and treatment of pulmonary emphysema, rheumatoid arthritis, osteoarthritis, and arteriosclerosis, among other diseases. The substituted amides oi the present invention may be represented by the following formulae:

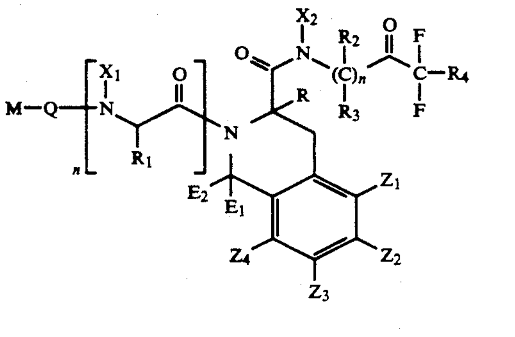

1A wherein

R is hydrogen or lower alkyl $R_1$, $R_2$, and $R_3$ are each selected independently from hydrogen, lower alkyl, substituted alkyl, aryl, aralkyl, substituted aralkyl, substituted aryl, or the side chains of naturally occurring alpha-amino acids. $R_1$, $R_2$, and $R_3$ may be lower alkyl groups containing from 1 to 12 carbons and may be substituted by the following groups: hydroxy; amino; alkoxy; alkenyl; alkynyl; alkylamino containing from 1 to 6 carbons; dialkylamino wherein each alkyl group contains from 1 to 6 carbons; alkanoyl containing from 1 to 6 carbons; arylcarbonyl wherein the aryl group contains 6, 10, or 12 carbons; aralkanoyl containing 8 to 13 carbons; amido which may be attached to the alkyl group via either the nitrogen or carbon of the amido, quanidino, carboxy, cycloalkyl (3-15 carbons); cycloalkyl-alkyl (4-12 carbons); heteroaryl; aryl which may optionally be partially hydrogenated; heteroalkyl; heteroarylalkyl; aryl containing 6, 10, or 12 carbons; bicycloalkyl; bicycloalkylalkyl; alkylureido; aralkylureido; arylureido; indanyl; or $R_2$ and $R_3$ taken together may form rings from three membered to six;

$R_4$ is hydrogen, halogen, $COR_5$, $CH_2COR_5$, $CONHCH(R_1)COR_5$, or $CONH(C)_d$

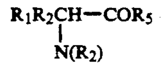

where d is an integer 1 to 6;

$R_5$ is hydroxy, lower alkoxy, arlkoxy, $NHR_1$, $NR_1$, $NR_1R_2$, naturally occurring alpha amino acid n is an integer, 1 to 2

$X_1$, $X_2$ is hydrogen, lower alkyl (1-6 carbons), cycoalkyl (3-9 carbons), cycloalkyl-alkyl, aralkyl, indanyl, bicycloakyl, bicycloakyl-alkyl, $E_1$, $E_2$ is hydrogen, lower alkyl, aralkyl, alkanoyl, aryl, carboxyalkyl, alkoxycarbonylalkyl, aminoalkyl. $E_1$ and $E_2$ taken together may form rings of three to seven members $Z_1$, $Z_2$, $Z_3$, and $Z_4$ are independently hydrogen, lower alkyl (1-6 carbons) lower alkoxy, lower aryloxy, alkylthio, halogen, nitro, cyano, amino, aminoalkyl, aminoalkanoyl, mercapto, thioalkyl, carboxy, hydroxy, alkoxycarbonyl, acetyl, formyl, alkanoyl, alkanoyloxy, alkylamino, or two adjacent Z groups taken together may form a methylenedioxy ring or a dioxalane ring.

Q is selected from the group consisting of

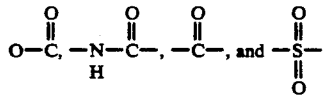

and

M is independently alkyl, substituted alkyl, cycloalkyl, substituted cycloalkyl, alkenyl, substituted alkenyl, aryl, substituted aryl, aralkyl, substituted aralkyl, an aliphatic heterocycle, substituted aralkyl, substituted aliphatic heterocycle, aromatic heterocycle or a substituted aromatic heterocycle, the above substituents may optionally be substituted by the following functionalities:

hydroxy; amino; alkylamino; dialkylamino; alkanoyl; arylcarbonyl; amido; alkylcarbonylamino; alkylaminocarbonyl; arylcarbonylamino; arylalkylcarbonylamino; arylaminocarbonyl; aralkylaminocarbonyl; carboxy; aryloxycarbonyl; aralkoxycarbonyl; alkanoyloxy; aroyloxy; aralkanoyloxy; alkylsulfonamido; cycloalkylsulfonamido; arylalkylsulfonamido; arylsulfonamido; acylsulfonamido; alkoxycarbonyl; and aralkoxycarbonylamino.

In particular, M is preferably selected from one of the following:

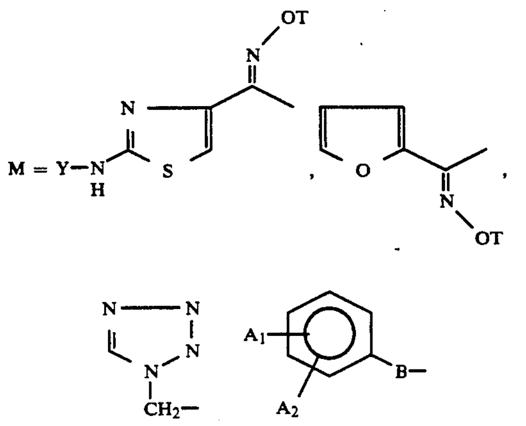

wherein $A_1$ and $A_2$ are hydrogen, lower alkyl, halogen, acetyl, or trifluoroacetyl, alkoxy, nitro, carboxy, cyano, and alkoxycarbonyl;

B is the group $—SO_2NHCO$ aryl; T is hydrogen, lower alkyl, C $(R)_nCOO_5$;

Y is H, lower alkyl, $—CO(CHR^1)_n\ COOR_6$; and n is an integer from 1 to 6

R' and $R_6$ are hydrogen or lower alkyl

The alkyl groups per se and in the alkyl moiety in aralkyl, cycloalkyl-alkyl, and the like and in alkoxy, alkylthio, alkanoyl and carbolkoxy may be straight chained or branched and are preferably lower alkyl groups containing from one to fifteen carbons. Such groups include methyl, ethyl, propyl, isopropyl, butyl, isobutyl, amyl, hexyl, and the like.

It is known to those skilled in the art that the tetrahydroisoquinoline amides of the present invention may have several asymmetric carbon atoms and thus may exist in several diastereomeric mixtures. The preferred compounds of the present invention are of the S-configuration which corresponds to the L-configuration of naturally occurring alpha-amino acids. The methods of synthesis described in Scheme A provide the products as a mixture of diastereomers, based upon the fact that the starting materials are (dl)-mixtures. To those skilled in the art, it is expected that the individual, separated diastereomers may not have the same biological activity, (e.g. one may be more active than the other). The present invention contemplates all diastereomeric mixtures as well as the active S and R forms.

As will be appreciated by those skilled in the art, the trifluoromethyl ketones and difluoromethyl ketones of the present invention may exist as solvates or in particular hydrates as is presented by the structure below. All these hydrates and solvates are encompassed within the scope of the present invention.

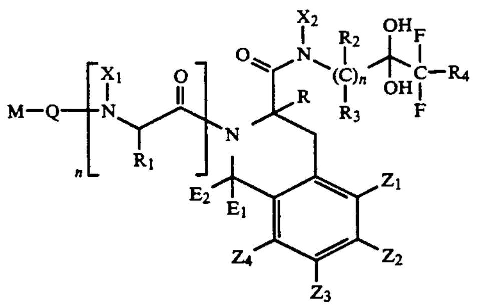

IB

To those skilled in the art it will be appreciated that starting materials for synthesis of the compounds of the present invention are derived from commercially available amino acids, and can be obtained from the following: glycine, alanine, valine, leucine, isoleucine, phenylalanine, norleucine, ornithine, tyrosine, tryptophan, glutamine, asparagine, aspartic acid, glutamic acid, lysine, arginine, serine, threonine, methionine, sarcosine, norvaline, histidine, α-aminobutyric acid, and phenylglycine. In particular, it will be appreciated by those skilled in the art of peptide synthesis that the $R_1$, $R_2$, and $R_3$, groups of structures IA and IB may be constructed from the side chains of naturally and commercially available alpha-amino acids.

The present invention describes the utilization of non-naturally occurring tetrahydroisoquinoline amino acids to obtain potent and specific inhibition of HNE and HLE both in vitro and in vivo. Unlike known inhibitors of HLE which embody proline as the penultimate C-terminal residue, the present invention utilizes exclusively non-naturally occurring tetrahydroisoquinoline amino acids to obtain potent and specific inhibition of HLE both in vitro and in vivo. This result is surprising and unexpected since it has previously been known that elastase prefers the naturally occurring amino acid proline at the P(II) subsite region, the residue in question. The nomenclature used for describing the individual amino acid residues ($P_1$, $P_2$, etc.) of a substrate and the subsites ($S_1$, $S_2$, etc.) of the enzyme is that of Schechter and Berger (Schechter, I. et al. *Biochem. Biophys. Res. Comm.*, 27, 157-162 (1967)). The potency of the compounds both, in vitro and in vivo, is unexpected also since it was previously known and established that elastase does not particularly like aromatic amino-acyl residues in the P(II) subsite region, as is present in the non-naturally occurring tetrahydrohydroisoquinoline amino acids of the present invention. It is also very surprising and unexpected that the inhibitors of the present invention are selective for elastase. This selectivity is unexpected since the natural substrate of elastase (elastin) contains a high percentage of the amino acid proline and the inhibitors of the present invention contain exclusively the non-naturally occurring amino acids of tetrahydroisoquinoline in place of proline. The in vitro potency and the in vivo data for the compounds of the present invention are unexpected in that the natural substrate of elastase contains a high percentage of proline residues.

The compounds of the present invention may be synthesized as follows:

Scheme A

The non-naturally occurring tetrahydroisoquinoline amino acids utilized in the present invention are normally prepared in one of two ways, Scheme A or B. The first method involves the treatment of an appropriately substituted benzyl halide 1 with ethyl acetoamidocyano acetate (2; D=CN) under basic conditions to give the intermediate 3. Hydrolysis and decarboxylation of 3 affords the amino acids 4 which are cyclized with aldehydes or ketones to give the tetrahydroisoquinoline alpha amino acids 5. The amino acids 5 are esterified with alcohols (e.g., EtOH, $CH_3OH$, $PhCH_2OH$) under standards methods to give the esters 6. Alternatively diethyl acetamidomalonate (2; D=COOEt) may be utilized in means similar to those described above and familiar to those skilled in the art of organic synthesis.

ously described above. A substituent alpha to the carboxy functionality of 8a (R=H) may be introduced through alkylation of 8a with R—X (X=halogen) under basic conditions to afford the intermediates 8b.

Scheme C

The required trifluoromethyl nitro alcohol 10 may be conveniently prepared by three different means, Schemes C, D and E. In Scheme C the appropriately substituted nitro compounds of formula $R_1CH_2NO_2$ are treated with trifluoroacetaldehyde or with commercially available trifluoroacetaldehyde ethyl hemiacetal of formula $CF_3CH(OH)OCH_2CH_3$ to give the nitro alcohols. The trifluoromethyl nitro alcohols 10 are obtained as a mixture of threo and erythro diastereomers. Normally the diastereomers are separated from one another at this stage by chromatography, crystallization, and/or both. The nitro compound 10 is reduced to the amino trifluoromethyl alcohol 11 by a variety of reducing agents which are familiar to those skilled in the art (e.g., $LiAlH_4$, catalytic hydrogenation, etc.). The amino 11 is normally isolated as its hydrochloride salt and is used directly without further purification.

SCHEME A

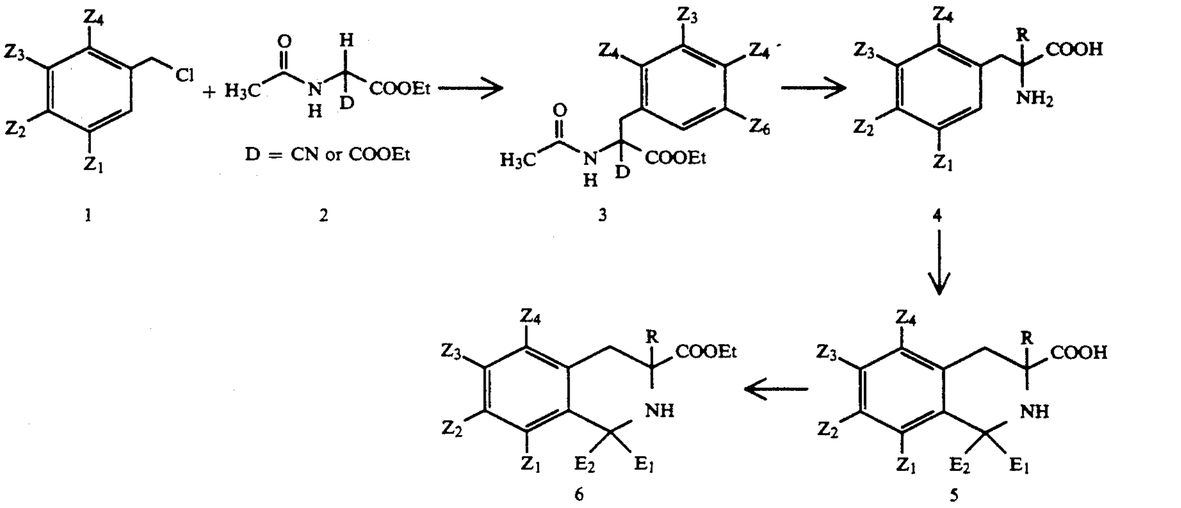

Scheme B

Alternatively the appropriately substituted benzyl halides 1 may be condensed under basic conditions (e.g., n-BuLi, LDA, or phase-transfer conditions) with the commercially available material 7 to give intermediates 8a. Mild hydrolysis of 8a (e.g., citric acid) affords the amino acid esters 9. Alternatively, treatment of 8a with mineral acids affords the amino acid 4 which may convert to the tetrahydroisoquinolines 5 by means previ-

SCHEME B

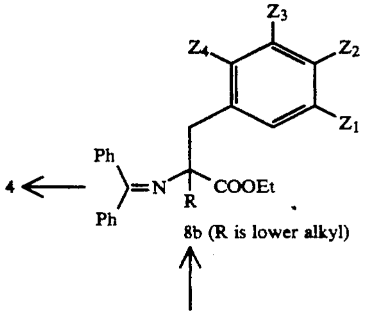
8b (R is lower alkyl)

-continued

SCHEME B

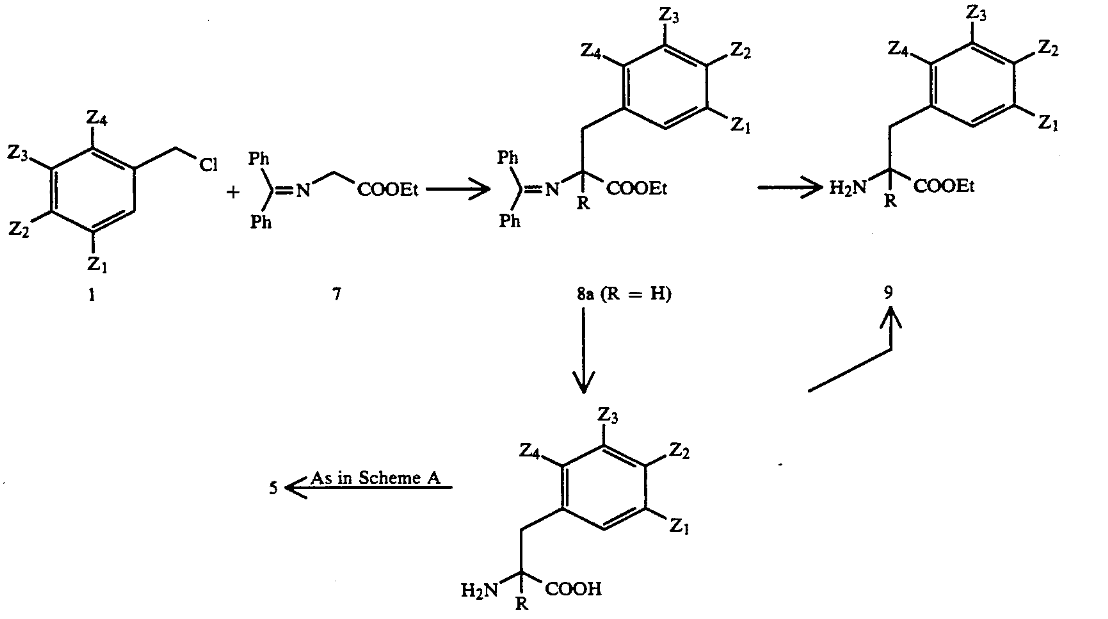

1 7 8a (R = H) 9

5

4 (R is hydrogen or lower alkyl)

SCHEME C $RCH_2NO_2 + CF_3CH(OH)OCH_2CH_3 \longrightarrow$

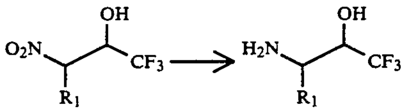

10 11

Scheme D

Alternatively the amino trifluoromethyl alcohols 11 can be obtained via a Curtius rearrangement. The synthesis is initiated with the readily available acids 12. The dianion of 12 is generated with LDA and then treated with trifluoroacetaldehyde to give the alcohol 13. The OH of the acid 13 is treated with TBDMS-OTF (tetrabutyldimethylsilyl triflate) to give the protected alcohol 14. The acid 14 is subjected to a Curtius rearrangement by employing DPPA (diphenylphosphoryl azide) in the presence of benzyl alcohol to give the CBZ - intermediate 15. The silyl protecting group of 15 is removed under standard methods familiar to those skilled in the art to give the CBZ - alcohols 16 which are subjected to hydrogenolysis conditions to give the amino alcohols 11.

Scheme E

Alternatively, protected amino acids such as 17 (PG=t-BOC CBZ, or FMOC) are condensed with dimethylhyroxylamine under standard methods familiar to those skilled in the art (e.g., DCC, WSCDI, CDI, mixed anhydride, etc.) to obtain the intermediate aldehydes 18. The amides 18 are reduced with $LiAIH_4$ to give the protected amino acid aldehydes 19. The aldehydes 19 are treated in THF with tetramethyl silane trifluoromethane (TMS—$CF_3$) and a catalytic amount of tetrabutylammonium fluoride ($n—Bu_4N^+F^-$) to give the trifluoromethyl silyl intermediates 20. The trifluoromethyl silyl compounds 20 are deprotected with aqueous hydrogen chloride to give the alcohols 21. The alcohols 21 are subjected to hydrogenolysis conditions, where PG=CBZ, to give the amino trifluoromethyl alcohols 11.

SCHEME D

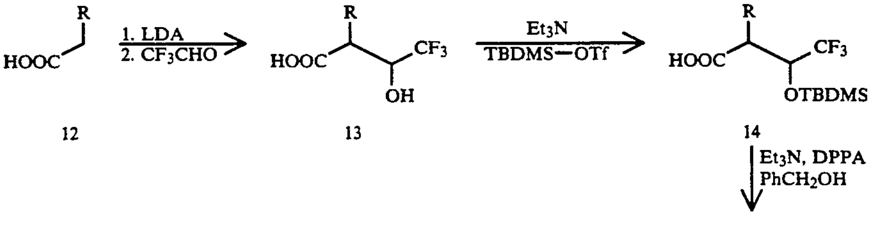

12 13 14

-continued

SCHEME D

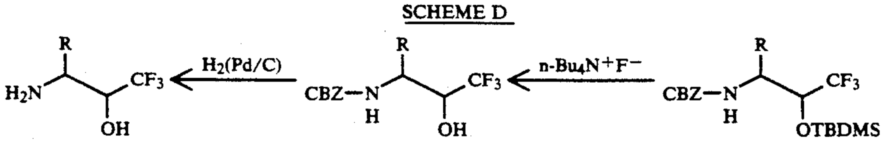

11 16 15

SCHEME E

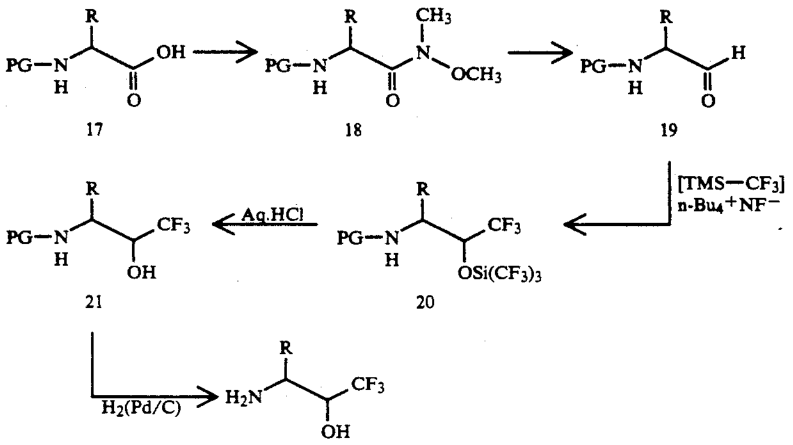

17 18 19 21 20 11

Scheme F

The non-naturally occurring tetrahydroisoquinolines 6 are condensed with the appropriately substituted N-protected alpha-amino acids 22 according to methods commonly used in peptide synthesis and familiar to those skilled in the art (e.g., M. Bodanszky and A. Bodanszky, "The Practice of Peptide Synthesis", Springer-Verlag, Berlin (1984); M. Bodanszky, "Principles of Peptide Synthesis", Springer-Verlag, Berlin (1984)) to give the non-naturally occurring dipeptide ester intermediates 23a. The intermediate ester 23a is deprotected under standard methods to give the acid 23b (R=H). The acid 23b is condensed by standard methods familiar to those skilled in the art with the amino trifluoromethyl alcohol 11 to give 24. The methods of protection and deprotection of amino acids and peptides described in the present invention are well known to those skilled in the art. In the present invention, for example, commonly used protecting groups for nitrogen can be either CBZ or tert-BOC although others are also contemplated (e.g., FMOC, TROC, etc.). The CBZ intermediates 24 are normally deprotected by catalytic hydrogenolysis whereas the tert-BOC group is removed by acid. Deprotection of the CBZ-intermediate 24 affords the intermediate amines. The intermediate amines resulting from deprotection of 24 are converted into intermediates 25 by their reaction with appropriate reagents for the formation of amides, ureas, urethanes, and sulfonamides including acid chlorides, anhydrides, isocyanates, chloroformates, sulfonyl chlorides, as would be familiar to those skilled in the art. Unless otherwise stated the intermediates 25 are usually obtained as a mixture of diastereomers. All diastereomers are within the scope of this invention. As would be known and appreciated by those skilled in the art the exact order of decoupling and condensation need not conform strictly to the order described above and may be altered. The intermediates 25 are oxidized to provide the products IA by PCC (pyridinium chloroformate), PDC (pridinium dichromate), oxalyl chloride/DMSO, Jones reagent, Collins reagent, etc. However the preferred method of oxidation is by utilization of the Dess-Martin periodane reagent which is commercially available. The utilization of this reagent has previously been described (D;B. Dess et al., *Journal of Organic Chemistry,* 48, 4455 (1983)).

To those skilled in the art it will be appreciated that the required trifluoromethyl alcohol 11 may also be obtained via, the Darkin - West reaction (H. D. Darkin and R. West, J. Biol. Chem., 78, 91, 745, and 757 (1928); E. J. Bourne, J. Burdon, V. C. R. McLoughlin et al., *J. Chem. Soc.,* 1771 (1961)).

SCHEME F
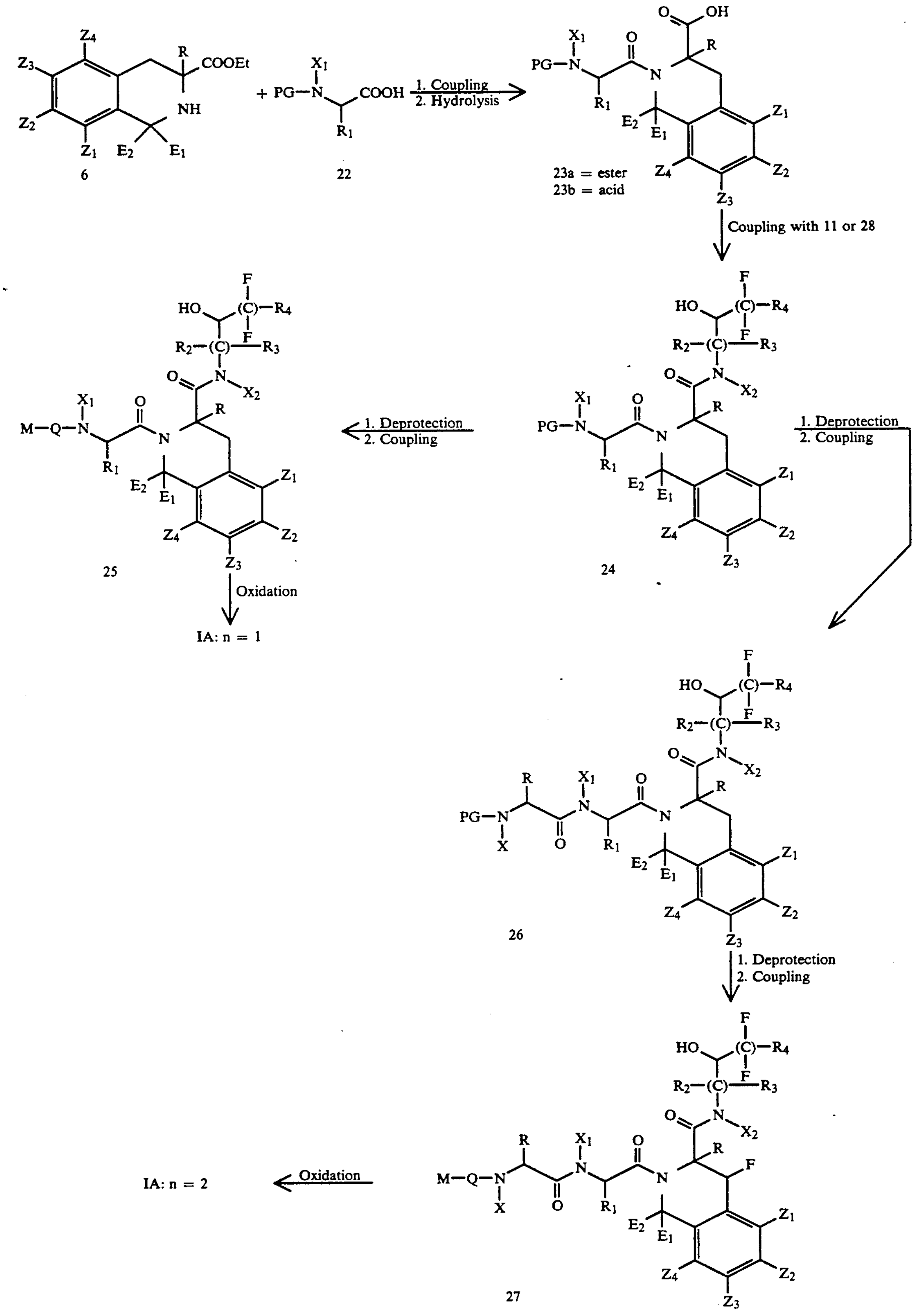
6
22
23a = ester
23b = acid
24
25
IA: n = 1
26
27
IA: n = 2

Scheme G

The synthesis of the difluoro products are prepared ideally via the aldehydes 19 of Scheme E. N-Protected commercially available alpha-amino acids (preferably tert-BOC) 17 are converted to the amino acid aldehydes 19 by a number of means familiar to those skilled in the art. One method, which is illustrated in Scheme E, involves the direct reduction of the amino acids 17 by known reducing agents (e.g., DIBAL; diisobutylaluminum hydride) to the corresponding aldehydes 19. Alternatively the acids 17 are reduced to the corresponding alcohols by known methods and then the alcohols are oxidized to the aldehydes 19 by known methods (e.g., Swern oxidation, PCC, etc.). The most desirable means of obtaining the aldehydes 19 involves the condensation of acids - with $HNCH_3(OCH_3)$ utilizing CDI (carbonyldiimidazole) as the condensing reagent to give the amides 18 as is illustrated in Scheme E. The amides 18 are reduced with $LiAlH_4$ to give the aldehydes 19. The aldehydes 19 are treated under Reformatsky reaction conditions, as is illustrated in Scheme G, with $BrC(F)_2COOR$ to give the intermediates 28. As will be appreciated by those skilled in the art of peptide synthesis and organic chemistry it is anticipated that the product resulting from the Reformatsky reaction of Scheme G may give rise to a number of possible diastereomers. All diastereomers are contemplated and are within the scope of this invention; however, the (SS)-diastereomer is preferred. The intermediates 28 are then condensed by methods familiar to those skilled in the art with the non-naturally occurring dipeptides 23a (described in Scheme F above) to give the amides 24. The amides 24 are transformed to I by methods analogous to those described above for Scheme F and familiar to those skilled in the art. As will be appreciated to those skilled in the art the exact order of the steps described in Scheme F may be altered. The esters IA ($R_4$=$CO_2R$) may be saponified by standard means to give the corresponding carboxylic acids (R=H).

SCHEME G

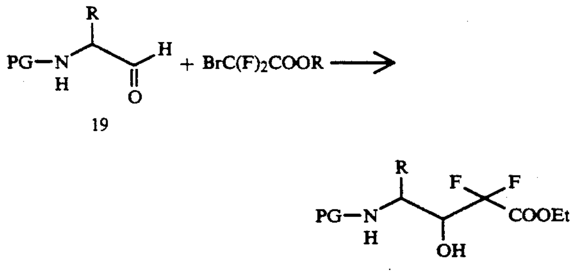

19

28

The compounds of the present invention are potent and specific inhibitors of HLE, as is demonstrated in the following tests.

Elastase Inhibition—In Vitro Method

The method of K. Nakajima et al., *Journal of Biological Chemistry*, 254: 4027–4032 was adapted to a microtiter format. The in vitro assay is based upon the hydrolysis of the commercially available (Sigma Chemical Company, St. Louis, Mo.) substrate methoxy O-succinyl-L-alanyl-L-alanyl-L-prolyl-L-valine para - nitroanilide (MeO-Suc-Ala-Ala-Pro-Val-pNA) and the release of para-nitroanilide (pNA), which absorbs at 405 nm.

Equipment a. Microtiter plates (96 wells, flat bottom)

b. Vmax Kinetic Microtiter Plate Reader, equipped with 405 nm filter (Molecular Devices)

c. Microtiter Plate Mixer (Fisher Scientific)

d. Spectrophotometer (e.g., Cary 118 for Ki and Km determinations)

Reagents a. Human sputum elastase (HSE) (Elasten Products Co., Pacific, Mo.) dissolved 1 mg/mL in 0.05M sodium chloride and frozen (50 μL aliquots) at −20° C. until used.

b. Stock solution of MeO-Suc-Ala-Ala-Pro-Val-pNA dissolved at 15 mM in dimethylsulfoxide (DMSO) and frozen (4 mL aliquots) at −20° C. until used.

c. Assay buffer: 0.1M tris buffer, pH 7.5 containing 0.5M sodium choloride.

Screening is performed in microtiter plates, using 0.5 mM substrate and monitored on a Microtiter Reader. Enzyme activity (+/− test compound) is determined as the rate of pNA release (linear regression analysis of slope). Inhibitory activity of the test compound is calculated relative to the uninhibited enzyme control, as follows:

$$\% \text{ Inhibition} = 100 - \frac{\text{rate (with test compound)}}{\text{rate (enzyme control)}}$$

A frozen aliquot of HSE is thawed and diluted with assay buffer to a stock concentration of 0.02 mg/mL (30× assay concentration). A frozen aliquot of the substrate stock solution is thawed and diluted to 0.5 mM with the assay buffer (final DMSO concentration is 10%). 10 μl of the test compounds stock solution (or assay buffer) and 10 μl of the HSE stock solution are pipetted into each microtiter well, in duplicate. The plate is mixed well, and pre-incubated at room temperature for 15 minutes. A 300 μl substrate solution is then added to each well and the $OD_{405}$ is followed for approximately 30 minutes.

The table below sets forth the results of in vitro testing with selected compounds of the present invention.

TABLE I (IN VITRO INHIBITION)

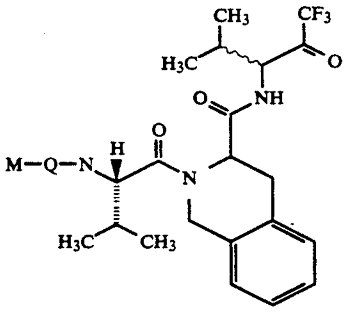

| M—Q | In Vitro $IC_{50}$ (ug/mL) |
|---|---|
| CBZ | 0-10 |
| p-[p-Cl($C_6H_4$)$SO_2$NHCO]($C_6H_4$)CO— | 0-082 |

Thus, the compounds of the present invention have demonstrated potent and specific in vitro inhibitory activity of HLE (of the order, $IC_{50}=0.082$ μg/mL) when assayed by the method described above.

Elastase Inhibition—Animal Model

When installed into the lungs of hamsters, purified preparations of HNE will produce an emphysema like state. Acute challenge (18 hours) with 50 μg of HNE results in pulmonary hemorrhage which can be readily quantified by measuring total RBC's (red blood count) and hemoglobin concentration of lung lavage samples. HNE (obtained from Elastin Products Co., Pacific, Mo.) was diluted to 250 μg/mL in 0.9% sterile saline. Syrian Golden Hamsters, males, weighing approximately 90–130 grams, were obtained from Charles River Laboratories. The experiments described below are conducted using at least three animals per group.

Anesthesia required for the intratracheal administration of compounds and elastase was induced by the i.p. injection of ketamine hydrochloride, 10 mg/100 gram body weight plus xylazine, 1 mg/100 gram body weight.

Hamsters were anesthetized as described above and the trachea were surgically exposed. Test compounds were administered via 27 gauge needle inserted directly into the trachea in 0.1 mL volume followed by a 0.1 mL saline push. Three to five minutes later 50 μg of HNE (0.2 mL) was administered via the same set-up followed by a 0.1 mL saline push. The animals were surgically closed. Eighteen hours later the animals were sacrificed by an overdose of pentobartitol, whole lung lavage were performed and assayed for hemoglobin concentration and cellular infiltration.

Lung lavage using 8 mL of saline yields 6.5 to 7.15 mL recovery per animal. Samples were mixed by inversion and 6 mL lavage fluid from each animal used for red blood cell (RBC) counts performed on a Coulter ZBI.

Samples were concentrated by centrifugation (1500 rpm, 10 minutes) and brought up to 1.0 mL in saline. Hemoglobin concentration was determined spectrophotometrically (540 nm) by the cyanmethemoglobin method using 200 ul sample to 2.5 mL cranmethoglobin reagent (Data Medical Associates, Arlington, Tex.).

The results of in vivo testing with the compounds of the present invention demonstrated their potential utility in an in vivo situation. The compounds of the present invention are effective elastase inhibitors that significantly prevent or diminish the severity of the enzyme-induced hemorrhage relative to the enzyme alone. In this in vivo model the compounds of the present invention inhibit the hemorrhage due to HNE (50 μg, i.t.) in the hamster by over 90% when administered 20 μg, i.t. As such the compounds of the present invention would be useful in the diagnosis and treatment of tissue degenerative diseases such as pulmonary emphysema, rheumatoid arthritis, adult respiratory distress syndrome - otherosclerosis, osteo arthritis, chronic obstructive lung disease, glomerular nephritis, inter alia.

The compounds of the present invention are unique in that they are composed of non-naturally occurring imino alphaamino acids. The compounds of this invention are very selective for HNE and HLE, and in general they do not inhibit other enzymes. These results are surprising and unexpected since the natural substrate of elastase is elastin which contains a high percentage of the naturally occurring amino acid L-proline. The table below illustrates the very high degree of selectivity that the inhibitors of the present invention possess.

DEMONSTRATION OF SELECTIVITY OF INHIBITORS

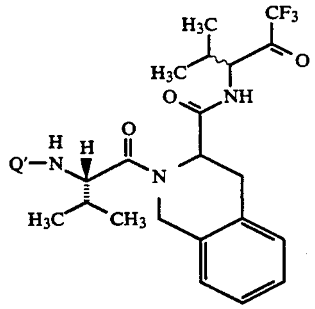

Q' is p—[p—Cl($C_6H_4$) $SO_2NHCO$]($C_6H_4$)CO—

| ASSAY | $IC_{50}$ (ug/mL) |
|---|---|
| Human Leukocyte Elastase | 0.082 |
| Thrombin | >>6 |
| Urokinase | >>6 |
| Human C1 Esterase | >>6 |
| Cathepsin B | >>6 |
| Plasmin | >>6 |
| Chymotrypsin | >>6 |
| Recombitant HIV Protease | >>50 |
| Recombitant 3C - Proteinase | >>50 |

Further, it is known to those skilled in the art that the biological activities of pharmaceutical agents may be diminished in vitro when human serum albumin (HSA) is added. This is due to the probable binding of compounds to protein. Blood plasma contains approximately 5% HSA. In the case of the present invention, however, the compounds of the present invention are just as active in vitro with or without a 5% HSA and thus would be expected not to bind to plasma protein in an in vivo situation in a diagnostic setting.

The compounds of the present invention may be administered for the alleviation of conditions which include tissue degenerative diseases such as: pulmonary emphysema, artherosclerosis and osteo- and rheumatoid arthritis, in particular emphysema, and other diseases. The mode of administration may be parenteral, including the subcutaneous deposit of an osmotic pump, or via a powered or liquid aerosol. For parenteral administration, an intraveneous, intramuscular, or subcutaneous injection would be given containing 0.02 to 10 mg/kg of compound of the invention two or four times daily. The injection would contain a compound of the invention in an aqueous isotonic sterile solution or optionally a suspension with a preservtive such as phenol or a solubilizing agent such as ethylenediamine tetraacetic acid (EDTA), and an aerosol. Compounds of the invention may also be administered in a similar manner via a Spinhaler(®). Each capsule to be use in the Spinhaler(®) contains the required amount of a compound of the invention with the remainder of the capsule being a pharmaceutically acceptable carrier.

By following the schemes and procedures described above, the following compounds, among others, may be prepared.

N-[3-(R,S)-[2-[4-[(4-Bromophenyl)sulfonylaminocarbonyl]phenylcarbonyl-L-valyl]-(6,7-dimethoxy-1,2,3,4-tetrahydroisoquinolyl)]carbonyl]-N-[3-(1,1,1-trifluoro-4-methyl-2-oxopentyl)]amine N-[3-(R,S)-[2-[4-[(4-Bromophenyl)sulfonylaminocarbonyl]-phenylcarbonyl-L-valyl]-(6,7-methylenedioxy-1,2,3,4-tetrahydroisoquinolyl)]carbonyl]-N-[3-(1,1,1-trifluoro-4-methyl-2-oxopentyl)]amine N-[3-[2-[2-Amino-α-(methoxyimino)-4-thiazoleacetyl-L-valyl]-(6,7-dimethoxy-1,2,3,4-tetrahydroisoquinolyl)]-carbonyl]-N-[3-(1,1,1-trifluoro-4-methyl-2-oxopentyl)]amine N-[3-[2-[2-Amino-α-(carboxymethoxyimino)-4-thiazolacetyl-L-valyl]-(5,6,7-trimethoxy-1,2,3,4-tetrahydroisoquinolyl)]carbonyl]-N-[3-(1,1,1-trifluoro-4-methyl-2-oxopentyl)]amine N-[3-(R,S)-[2-[4-[(4-Bromophenyl)sulfonylamino-carbonyl]phenylcarbonyl-L-valyl]-(6,7-dimethoxy-1,1-dimethyl-1,2,3,4-tetrahydroisoquinolyl)]carbonyl]-N-[3-(1,1,1-trifluoro-4-methyl-2-oxopentyl)]amine N-[3'-(R,S)-[2'-[4-[(4-Bromophenyl)sulfonylaminocarbonyl]phenylcarbonyl-L-leucyl]-spiro[cyclopentane-1,1'-(6.7-dimethoxy-1,2,3,4-tetrahydroisoquinolyl)]]-carbonyl]-N-[3-(1,1,1-trifluoro-4-methyl-2-oxopentyl)]amine N-[3-(R,S)-[2-[4-[(4-chlorophenyl)sulfonylamino-carbonyl]phenylcarbonyl-L-leucyl]-(1-benzyl -5,6,7-trimethoxy-1,2,3,4-tetrahydroisoquinolyl)]carbonyl]-N-[3-(1,1,1-trifluoro-4-methyl-2-oxopentyl)]amine N-[3'-(R,S)-[2'-[2-Amino-α-(methoxyimino)-4-thiazolacetyl-L-valyl]-spiro[cyclohexane -1,1'-(6,7-dimethoxy-1,2,3,4-tetrahydroisoquinolyl)]]carbonyl]-N-[3-(1,1,1-trifluoro-4-methyl-2-oxopentyl)]amine N-[3'-(R,S)-[2'-[2-(methoxysuccinyl)amino-α-(methoxyimino)-4-thiazolacetyl-L-valyl(6,7-dimethoxy-1,2,3,4-tetrahydroisoquinolyl)]carbonyl]-N-[3-(1,1,1-trifluoro-4-methyl-2-oxopentyl)]amine N-[3-(R,S)-[2-[4-[(4-chlorophenyl)sulfonylaminocarbonyl]phenylcarbonyl-L-valyl]-3-methyl -1,2,3,4-tetrahydroisoquinolyl)]carbonyl]-N-[3-(1,1,1-trifluoro-4-methyl-2-oxopentyl)]amine N-[3-(R,S)-[2-[4-[(4-Bromophenyl)sulfonylaminocarbonyl]phenylcarbonyl-L-valyl]-(6,7-dimethoxy-1,2,3,4-tetrahydroisoquinolyl)]carbonyl]-N-[3-(1,1-difluoro-2-oxo-4-methyl-1-aminocarbonylpentyl)]

N-[3-(R,S)-[2-[4-[(4-chlorophenyl)sulfonylaminocarbonyl]phenylcarbonyl-L-valyl]-(1,2,3,4-tetrahydroisoquinolyl)]carbonyl]-N-[3-(1,1-difluoro-2-oxo-4-methyl-1-carboxyl-pentyl)]

N-[3'-(R,S)-[2'-[(2-methoxysuccinyl)amino-α-(methoxycarboxy)-4-thiazole-acetyl)-L-valyl]-(6,7-dimethoxy-1,2,3,4-tetrahydroisoquinolyl)]carbonyl]-N-[3-(1,1-difluoro-2-oxo-4-methyl-1-aminocarbonylpentyl)]

N-[α-(methoxyimino)-2-furylacetyl-L-valyl]-(6,7-dimethoxy-1,2,3,4-tetrahydroisoquinolyl)]carbonyl]-N -[3-(1,1,1-trifluoro-4-methyl-2-oxopentyl)]amine 2-Methyl-1-nitropropane 1-Iodo-2-methylpropane (92.0 g; 0.5 mole) was dissolved in anyhdrous diethyl ether (50 mL) and added dropwise to a precooled (020 -3° C.) suspension of silver nitrite (98.5 g; 0.64 mole) in ether (200 mL). The reaction mixture was protected from light and allowed to stir by means of a mechanical stirrer at room temperature until a negative copper flame test indicated the completion of the reaction (3–6 days). The mixture was filtered through Celite and the ether was evaporated. The remaining liquid was distilled to yield (38.9 g; 75.5%) of a clear liquid boiling at 55°–60° C. @=50 mm Hg. (Caution: nitro compound° ).

Threo-[(SS)+(RR)]-4-Methyl-3-nitro-1,1,1-trifluoro-2-pentano 1

2-Methyl-1-nitropropane (38.9 g, 0.377 mole), trifluoroacetaldehyde ethylhemiacetal (60.4 g; @90%, 0.377 mole) and $K_2CO_3$ (2.15 g, 0.0156 mole) were mixed and stirred at 60° C. for 3 hours followed by 3 days at room temperature. A saturated aqueous solution of NaCl (75 mL) was added followed by 1N HCl (50 mL). The organic layers were separated. The aqueous layer was washed twice with 250 mL of ether and the organic layers were combined and washed with a saturated NaCl solution. After drying over $MgSO_4$ and filtration the ether was evaporated under reduced pressure and the residue was placed in a freezer* where the threoproduct crystallized. The solid was filtered and washed with cold petroleum ether (bp 37°–50° C.). Yield 21.8 g, 28.8%. TLC, Rf=0.62, silica gel, $CH_2Cl_2$: $CH_3OH$ (97:3). The filtrate contains the erythro product isolated as a colorless oil.

*The residue could also be chromatographed over silica gel using a gradient elution of $CH_2Cl_2$:hexane 50:50 to 75:25 to pure $CH_2Cl_2$.

Threo

](SS)+(RR)]-3-Amino-4-methyl-1,1,1-trifluoro-2-pentanol hydrochloride

The threo-nitro compound above (21.8 g, 0.108 mole) was dissolved in ether and added dropwise to a suspension of lithium aluminium hydride (13 g, 0.343 mole) under nitrogen. After addition the reaction mixture was allowed to stir at room temperature for 1 hour before the excess $LiAlH_4$ was carefully destroyed with an aqueous staturated solution of potasium bisulfate. The resulting suspension was filtered through Celite and the filtrate was treated with anhydrous ether which was previously saturated with anhydrous hydrogen chloride. After evaporation of the ether a sticky oil remained which upon repeated treatment with either yielded a white solid (11 g; 0.053 mole, 49%) melting at 123°–125° C.

(Analysis calc. for $C_6H_{12}F_3NO \times HCl$: c: 34.71, H: 6.31, N: 6.75;

Found: C: 34.54, H: 6.36, N: 6.71).

Terephthalic Acid-Di-Tert-Butyl Ester

Terephthaloyl chloride (50.8 g, 0.25 mole) was suspended in tetrahydrofuran (400 mL) and tert-butanol (55.8 g, 0.75 mole) was added followed by pyridine (39.6 g, 0.5 mole). After an initially slightly exothermic reaction the mixture was allowed to stir over night at room temperature. The white solid (pyridinium hydrochloride) was filtered and the filtrate evaporated. The residue was treated with water and the resulting white solid filtered and recrystallized from methanol (hot filtration from insoluble material to yield a whiche solid.* (54.3 g, 78%) mp. 116°–118° C.

*In some experiments a mixture of mono-and di-tert-butyl ester was isolated and used as is for saponification after determining the ratios.

Terephthalic Acid-Mono-T-Butyl Ester

A slurry of terephthalic acid di-tert-butyl ester (6.1 g, 0.022 mole) in tert-butanol (30 mL) was added to 1N KOH (22 mL, 0.022 mole). The mixture was heated to 60° C. for 7–8 hours. After cooling the mixture was treated with water and extracted 3 times with ethyl acetate. The aqueous layer was acidified with diulute HCL and the product was extracted into ethyl acetate. After washing of the organic layer with a saturated aqueous NaCl solution and drying over $MgSO_4$, the solvent was filtered and concentrated to yield terephthalic acid mono tert-butyl ester as a white solid (4.7 g, 96%) melting at 100°-102° C.

1,1-Dimethylethyl-4-](4-Chlorophenyl)sulfonylaminocarbonyl]benzoate

The following reaction is conducted under nitrogen utilizing a mechanical stirrer. Terephthalic acid mono-tert-butyl ester (7.7 g, 0.0346 mole) was added to $CH_2Cl_2$ (25 mL) followed by dimethylaminopyridine (4.23 g, 0.0346 mole) and 4-chlorobenzenesulfonamide (6.64 g, 0.0346 moles). In portions WSCDI, 1-(3-dimethylaminopropyl)-3-ethylcarbodiimide hydrochloride (6.64 g, 0.0346 mole) was added and a total of 125 mL $CH_2Cl_2$ was used to wash down the reagent. The reaction was allowed to stir over night at room temperature whereby the suspended solids dissolved. The reaction was evaporated to dryness under reduced pressure and the residue treated with water and ethyl acetate. The organic layer was washed with 20% aqueous citric acid, saturated aqueous $NaHCO_3$ and saturated NaCl. After drying over $MgSO_4$ followed by filtration and evaporation a solid was obtaind which was treated with ether and filtered to yield 1,1-dimethylethyl-4-[(4-chlorophenyl)sulfonylaminocarbonyl]benzoate (5.8 g, 42.3%) as a white solid (mp: above 300° C.) which was used for hydrolysis.

4-](4-Chlorophenyl)sulfonylaminocarbonyl]benzene carboxylic acid

Trifluoroacetic acid (66 mL) was placed in a flask equipped with a drying tube ($CaCl_2$) and mechanical stirrer. After cooling to 0° C. the tert-butyl ester above from the previous experiment was added in portions. After initially going into solution the reaction mixture formed a heavy white precipitate. After 2 hours of vigorous stirring at 0° C. the mixture was poured onto ice/water and stirred for 2 hours before being filtered, washed with water and dried to yield a white solid. Recrystallization from ethanol/water (1:1) gave the product 4-[(4-Chlorophenyl)sulfonylaminocarbonyl] benzene carboxylic acid in 63% yield melting at 285°-287° C.

Ethyl N-Carbobenzyloxy-L-Valyl-1,2,3,4-tetrahydro-3-isoquinoline carboxylate

CBZ-L-Valine (12.6 g, 0.05 mol) and triethylamine (5.06 g 0.05 mol) were dissolved in THF (100 mL) and then cooled to 0°-5° C, with an ice water bath. Ethyl chloroformate (5.44 g, 0.05 mol) in THF (35 mL) was added dropwise at 0°-5° C. Following the addition the mixture was stirred for one hour in the cold. Ethyl 1,2,3,4-tetrahydroisoquinoline-3-carboxylate hydrochloride (14.5 g, 0.06 mol) and triethylamine (6.1 g, 0.06 mol) in $CH_2Cl_2$ (60 mL) and THF (30 mL) were added at 0° C. The reaction mixture as allowed to sit at room temperature overnight. Evaporation of the solvent yielded a viscous semisolid which was treated with ethyl acetate followed by 1N HCl and the layers were separated. The organic extract was washed with 1N aqueous HCl followed by 5% aqueous $Na_2CO_3$ and saturated aqueous NaCl-solution. After drying over $MgSO_4$, filtration and evaporation under reduced pressure afforded an oil (12.5 g) which was purified over silica gel using hexane: ethyl acetate (8:2) as eluent. Collected 2.9 g of the desired product as a viscous oil.

Analysis calc. for $C_{25}H_{30}N_2O_5$: C, 68.44; H, 6.90; N, 6.39.

Found: C, 67.94; H, 6.87; N, 6.16.

N-CBZ-L-Valyl-N-1,2,3,4-tetrahydro-3-isoquinolinecarboxylic acid

Ethyl N-CBZ-L-valyl-N-1,2,3,4-tetrahydro-3-isoquinolinecarboxylate (2.58 g, 5.9 mmol) was dissolved in ethanol (35 mL) and treated with 1N aqueous KOH (7.4 mL) in portions of 1.0 mL at 0°-5° C. The mixture was allowed to sit at room temperature overnight. The ethanol was removed under reduced pressure, and the residue was treated with water. The product was extracted three times into ethyl acetate and afterwards the aqueous layer was acidified with 2N aqueous HCl. The product was extracted into ethyl acetate and washed with saturated aqueous sodium chloride. The organic extract was dried over $MgSO_4$ and filtered. Evaporation of the solvent under reduced pressure afforded the product as a white semisolid (1.7g).

Analysis calc. for $C_{23}H_{26}N_2O_5$: C, 66.57; H, 6.44; N, 6.75.

Found: C, 66.34; H, 6.46; N, 6.55.

N-CBZ-L-Valyl-N-[3-(1,1,1-trifluoro-4-methyl-2-hydroxypentyl)]-1,2,3,4-tetrahydro-3-isoquinolinecarboxamide N-CBZ-L-Valyl-N-1,2,3,4-tetrahydro-3-isoquinolinecarboxylic acid (2.8 g, 6.82 mmol) was dissolved in THF (50 mL) and 1,1'-carbonyldiimidazole (1.11 g, 6.82 mmol) was added. After two hours of stirring at room temperature a suspension of 3-amino-4-methyl-1,1,1-trifluoro-2-pentanol hydrochloride salt (1.45 g, 7.0 mmol) and triethylamine (0.7 g, 7.0 mmol) in THF (25 mL) was added. The mixture was allowed to sit overnight and afterwards it was concentrated under vacuum. The remaining residue was treated with ethyl acetate and washed sequentially with 1N aqueous HCl, 5% aqueous $Na_2CO_3$ and saturated aqueous NaCl solutions. The organic extract was dried over $MgSO_4$, filtered and evaporated to yield a semisolid which was purified over silica gel utilizing $CH_2Cl_2$:$CH_3OH$ (97:3) as eluent. Collected 2.5 g solid melting at 76°-79° C.

Analysis calc. for $C_{29}H_{36}F_3N_3O_5$: C, 60.80; N, 7.46.

Found C, 60.84; H, 6.45; N, 7.25.

L-Valyl-N-[3-(1,1,1-trifluoro-4-methyl-2-hydroxypentyl)]-1,2,3,4-tetrahydro-3-isoquinolinecarboxamide N-CBZ-L-Valyl-N-[3-(1,1,1-trifluoro-4-methyl-2-hydroxypentyl)]-1,2,3,4-tetrahydro-3-isoquinolinecarboxamide (0.5 g, 0.887 mmol) was dissolved in absolute ethanol (20 mL) and catalytic amounts of palladium on carbon (10%) were added. The mixture was allowed to shake on a Parr Hydrogenator at 45-50 pounds per square inch hydrogen pressure for several hours. The mixture was filtered through a pad of Celite and the ethanol was evaporated under reduced pressure. Obtained 0.4 g of a semisolid which was used without further purification for the next reaction.

[[4-(4-Chlorophenyl)sulfonylaminocarbonyl]phenyl-1-oxomethyl]-L-valyl-N-[3-(1,1,1-trifluoro-4-methyl-2-hydroxypentyl)]1,2,3,4-tetrahydro-3-isoquinolinecarboxamide The following reactants were mixed in the stated order in dry THF (35 mL) at 0°-5° C. L-Valyl-N-[3-(1,1,1-trifluoro-4-methyl-2-hydroxypentyl)]-1,2,3,4-tetrahydro-3-isoquinolinecarboxamide (0.52 g, 1.21 mmol), HOBT (0.15 g, 1.1 mmol), 4-[(4-chlorophenyl)-sulfonylaminocarbonyl]benzene carboxylic acid (0.37 g, 1.1 mmol), and WSCDI (0.45 g, 1.21 mmol). The mixture was stirred at 0°-5° C. for 30 minutes and then allowed to warm up to room temperature over a period of four hours. The THF was evaporated under vacuum and the residue treated with ethyl acetate and washed with 1N aqueous HCl, 5% aqueous $Na_2CO_3$ and saturated aqueous NaCl. The organic extract was dried over $MgSO_4$, filtered and evaporated to dryness. The residue was purified over silica gel using 97:3 followed by 90:10 $CH_2Cl_2$: $CH_3OH$ as eluent. Collected 0.45 g solid melting at 228°-232° C.

[[4-(4-Chlorophenyl)sulfonylaminocarbonyl]phenyl-1-oxomethyl]-L-valyl-N-[3-(1,1,1-trifluoro-4-methyl-2-oxopentyl)]-1,2,3,4-tetrahydro-3-isoquinoline-carboxamide.

[[4-(4-Chlorophenyl)sulfonylaminocarbonyl]phenyl-1-oxomethyl]-L-valyl-N-[3-(1,1,1-trifluoro-4-methyl-2-hydroxypentyl)]-1,2,3,4-tetrahydro-3-isoquinolinecarboxamide (0.33 g, 0.44 mmol) was added to $CH_2Cl_2$ (15mL) followed by Dess-Martin periodinane (0.56 g, 1.3 mmol) in $CH_2Cl_2$ (20 mL). Trifluoroacetic acid (0.15 g, 1.3 mmol) was slowly added and the reaction mixture allowed to stir at room temperature overnight. The solvents were evaporated off under vacuum and the residue treated with a mixture of ethyl acetate and saturated aqueous solutions of $NaHCO_3$ and $Na_2S_2O_3$. The organic layer was separated and washed repeatedly with solutions of dilute aqueous $NaHCO_3$ and $Na_2S_2O_3$. After a final wash with brine the organic extract was dried over $MgSO_4$, filtered and evaporated to afford a solid, which was purified over silica gel using a gradient elution with $CH_2Cl_2$: $CH_3OH$ 97:3, 90:10. Yield 0.23 g, mp: 165°-172° C.

Analysis calc. for $C_{35}H_{36}ClF_3N_4O_7S$: C, 56.11; H, 4.84; N, 7.48; S, 4.28.

Found: C, 55.73; H, 4.98; N, 7.14; S, 4.63.

What is claimed is:

1. A compound of the following formula

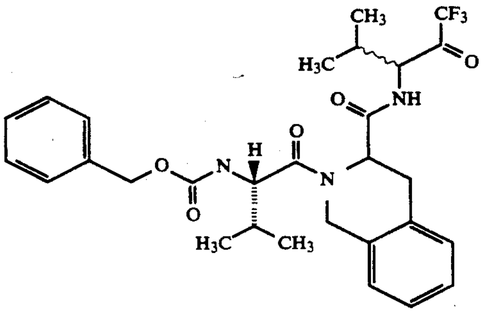

2. A compound of the following formula:

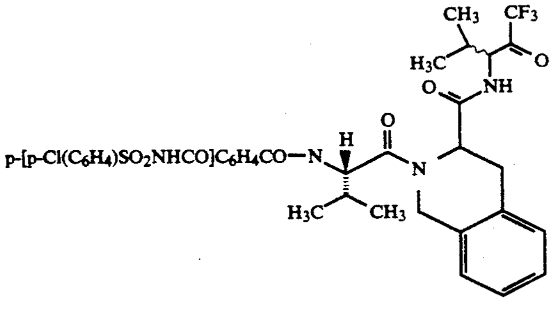

3. A compound selected from the group consisting of:

N-[3-(R,S)-[2-[4-[(4-Bromophenyl)sulfonylaminocarbonyl]phenylcarbonyl-L-valyl]-(6,7-dimethoxy -1,2,3,4-tetrahydro-isoquinolyl)carbonyl]-N-[3-(1,1,1-trifluoro-4-methyl-2-oxopentyl)]amine N-[3-(R,S)-[2-[4-[(4-Bromophenyl)sulfonylaminocarbonyl]-phenylcarbonyl-L-valyl]-(6,7-methylene-dioxy-1,2,3,4-tetrahydroisoquinolyl)]carbonyl]-N-[3-(1,1,1-trifluoro-4-methyl-2-oxopentyl)]amine N-[3-[2-[2-Amino-α-(methoxyimino)-4-thiazoleacetyl-L-valyl]-(6,7-dimethoxy-1,2,3,4-tetrahydroisoquinolyl)]carbonyl]-N-[3-(1,1,1-trifluoro-4-methyl-2-oxopentyl)]amine N-[3-[2-[2-Amino-α-(carboxymethoxyimino)-4-thiazolacetyl-L-valyl]-(5,6,7-trimethoxy-1,2,3,4-tetrahydroisoquinolyl)]carbonyl]-N-[3-(1,1,1-trifluoro-4-methyl-2-oxopentyl)]amine N-[3-(R,S)-[2-[4-[(4-Bromophenyl)sulfonylaminocarbonyl]phenylcarbonyl-L-valyl]-(6,7-dimethoxy -1,1-dimethyl-1,2,3,4-tetrahydroisoquinolyl)]carbonyl]-N-[3-(1,1,1-trifluoro-4-methyl-2-oxopentyl)]amine N-[3'-(R,S)-[2'-[4-[(4-Bromophenyl)sulfonylaminocarbonyl]phenylcarbonyl-L-leucyl]-spiro [cyclopentane-1,1'-(6,7-dimethoxy-1,2,3,4-tetrahydroisoquinolyl)]-carbonyl]-N-[3(1,1,1-trifluoro -4-methyl-2-oxopentyl)]amine N-[3-(R,S)-[2-[4-[(4-chlorophenyl)sulfonylaminocarbonyl]phenylcarbonyl-L-leucyl]-(1-benzyl -5,6,7-trimethoxy-1,2,3,4-tetrahydroisoquinolyl)]-carbonyl]-N-(3-(1,1,1-trifluoro-4-methyl-2-oxopentyl) ]amine N-[3'-(R,S)-[2'-[2-Amino-α-(methoxyimino)-4-thiazolacetyl-L-valyl]-spiro[cyclohexane -1,1'-(6,7-dimethoxy-1,2,3,4-tetrahydroisoquinolyl)]carbonyl]-N-[3-(1,1,1-trifluoro-4-methyl -2-oxopentyl)]amine N-[3'-(R,S)-[2'-[2-(methoxysuccinyl)amino-α-(methoxyimino)-4-thiazolacetyl-L-valyl(6,7-dimethoxy-1,2,3,4-tetrahydroisoquinolyl)]carbonyl]-N-[3-(1,1,1-trifluoro-4-methyl-2-oxopentyl)]amine N-[3-(R,S)-[2-[4-[(4-chlorophenyl)sulfonylaminocarbonyl]phenylcarbonyl-L-valyl]-3-methyl -1,2,3,4-tetrahydroisoquinolyl)]carbonyl]-N-[3-(1,1,1-trifluoro-4-methyl-2-oxopentyl)]amine N-[3-(R,S)-[2-[4-[(4-Bromophenyl)sulfonylaminocarbonyl]phenylcarbonyl-L-valyl]-(6,7-dimethoxy -1,2,3,4-tetrahydroisoquinolyl)]carbonyl]-N-[3-(1,1-difluoro-2-oxo-4-methyl-1-aminocarbonylpentyl)]

N-[3-(R,S)-[2-[4-[(4-chlorophenyl)sulfonylaminocarbonyl]phenylcarbonyl-L-valyl]-(1,2,3,4-tetrahydroisoquinolyl)]carbonyl]-N-[3-(1,1,-difluoro-2-oxo-4-methyl-1-carboxyl-pentyl)]

N-[3'-(R,S)-[2'-[(2-methoxysuccinyl)amino-α-(methoxycarboxy)-4-thiazole-acetyl)-L-valyl]-(6,7-dimethoxy-1,2,3,4-tetrahydroisoquinolyl)]carbonyl]-N-[3-

(1,1-difluoro-2-oxo-4-methyl-1-aminocarbonylpentyl)]

N-[α-(methoxyimino)-2-furylacetyl-L-valyl]-(6,7-dimethoxy-1,2,3,4-tetrahydroisoquinolyl)]carbonyl]-N -[3-(1,1,1-trifluoro-4-methyl-2-oxopentyl)]amine 4. A pharmaceutical composition of matter comprising the compound as recited in claim 1 together with a pharmaceutically acceptable carrier.

5. A method of treating diseases in warm-blooded animals caused or induced by elastases which comprises administering to said animals a therapeutically effective amount of the compound as recited in claim 1.

6. A pharmaceutical composition of matter comprising the compound as recited in claim 2 together with a pharmaceutically acceptable carrier.

7. A method of treating diseases in warm-blooded animals caused or induced by elastases which comprises administering to said animals a therapeutically effective amount of the compound as recited in claim 6.

8. A pharmaceutical composition of matter comprising one or more compounds as recited in claim 3 together with a pharmaceutically acceptable carrier.

9. A method of treating diseases in warm-blooded animals caused or induced by elastases which comprises administering to said animals a therapeutically effective amount of one or more compounds as recited in claim 3.

* * * * *